(12) United States Patent
Belov et al.

(10) Patent No.: US 6,958,473 B2
(45) Date of Patent: Oct. 25, 2005

(54) A-PRIORI BIOMARKER KNOWLEDGE BASED MASS FILTERING FOR ENHANCED BIOMARKER DETECTION

(75) Inventors: Mikhail Belov, Burlingame, CA (US); Peter Foley, Los Altos, CA (US)

(73) Assignee: Predicant Biosciences, Inc., South San Francisco, CA (US)

(*) Notice: Subject to any disclaimer, the term of this patent is extended or adjusted under 35 U.S.C. 154(b) by 0 days.

(21) Appl. No.: 10/810,332

(22) Filed: Mar. 25, 2004

(65) Prior Publication Data

US 2005/0211891 A1    Sep. 29, 2005

(51) Int. Cl.[7] .............................................. H01J 49/34
(52) U.S. Cl. ....................................................... 250/282
(58) Field of Search .............................. 250/282, 281, 250/291, 292

(56) References Cited

U.S. PATENT DOCUMENTS

| | | |
|---|---|---|
| 4,963,736 A | 10/1990 | Douglas et al. |
| 4,977,320 A | 12/1990 | Chowdhury et al. |
| 5,045,694 A | 9/1991 | Beavis et al. |
| 5,245,186 A | 9/1993 | Chait et al. |
| 5,396,065 A | 3/1995 | Myerholtz et al. |
| 5,545,304 A | 8/1996 | Smith et al. |
| 5,572,022 A | 11/1996 | Schwartz et al. |
| 5,834,771 A | 11/1998 | Yoon et al. |
| 5,917,185 A | 6/1999 | Yeung et al. |
| 5,939,612 A | 8/1999 | Wylie et al. |
| 5,994,695 A | 11/1999 | Young |
| 6,075,244 A | 6/2000 | Baba et al. |
| 6,091,502 A | 7/2000 | Weigl et al. |
| 6,107,625 A | 8/2000 | Park |
| 6,107,628 A | 8/2000 | Smith et al. |
| 6,175,112 B1 | 1/2001 | Karger et al. |
| 6,207,954 B1 | 3/2001 | Andrien, Jr. et al. |
| 6,300,626 B1 | 10/2001 | Brock et al. |
| 6,305,975 B1 | 10/2001 | Steiner |
| 6,316,768 B1 | 11/2001 | Rockwood et al. |
| 6,369,383 B1 | 4/2002 | Cornish et al. |
| 6,437,325 B1 | 8/2002 | Reilly et al. |
| 6,465,776 B1 | 10/2002 | Moini et al. |
| 6,495,016 B1 | 12/2002 | Nawracala |
| 6,521,887 B1 | 2/2003 | Funsten et al. |
| 6,541,768 B2 | 4/2003 | Andrien, Jr. et al. |
| 6,614,020 B2 | 9/2003 | Cornish |
| 6,744,046 B2 | 6/2004 | Valaskovic et al. |
| 6,803,564 B2 | 10/2004 | Kawato |
| 2002/0054289 A1 | 5/2002 | Thibault et al. |

(Continued)

OTHER PUBLICATIONS

Brock, Ansgar, et al., "Hadamard transform time-of-flight mass spectrometry". Anal. Chem. (1998) 70:3735-3741.

(Continued)

*Primary Examiner*—Kiet T. Nguyen
(74) *Attorney, Agent, or Firm*—Wilson Sonsini Goodrich & Rosati (57) ABSTRACT

Methods and apparatus for mass filtering based on a-priori biomarker knowledge and elution time intervals for selected ion species from a separation device. A sample may be screened for biomarker patterns based on distinct elutions times for selected ions or peptides. A mass spectrum for species of interest can be tailored by filtering out undesired ions by measuring corresponding elution times and determining a priori selected elution time intervals for desired ion species only. The invention assists in the identification of biomarkers having known mass spectral peaks corresponding to known proteins or ions of interest that are known to elute from a separation device within a pre-defined elution time window.

14 Claims, 5 Drawing Sheets

U.S. PATENT DOCUMENTS

| | | | |
|---|---|---|---|
| 2003/0034449 | A1 | 2/2003 | Miller et al. |
| 2003/0052269 | A1 | 3/2003 | Apffel, Jr. et al. |
| 2003/0071206 | A1 | 4/2003 | Belov et al. |
| 2003/0146377 | A1 | 8/2003 | Miller et al. |
| 2003/0146392 | A1 | 8/2003 | Kimmel et al. |
| 2004/0089803 | A1 | 5/2004 | Foley |
| 2004/0159783 | A1 | 8/2004 | Gavin et al. |
| 2004/0183007 | A1 | 9/2004 | Belov et al. |
| 2004/0195500 | A1 * | 10/2004 | Sachs et al. ............... 250/282 |

OTHER PUBLICATIONS

Covey, Thomas R., et al., "Structural characterization of protein tryptic peptides liquid via chromatography/mass spectrometry and collision-induced dissociation of their doubly charged molecular ions". Anal. Chem. (1991), 63:1193-1200.

Fernandez, Facundo M., et al., "Hadamard transform time-of-flight mass spectrometry: a high-speed detector for capillary-format separations". Analytical Chemistry (Apr. 1, 2002), 74(7)1611-1617.

Geromanos, S. et al., "Tuning of an electrospray ionization source for maximum peptide-ion transmission into a mass spectrometer", Analytical Chemistry (2000), 72(4), 777-790.

Mlynski, V. et al., "Matrix-assisted laser/desorption ionization time-of-flight mass spectrometer with orthogonal acceleration geometry: preliminary results". Rapid Communications in Mass Spectrometry (1996) 10:1524-1530.

OTOF Description, Pacific Northwest Laboratory, printed from Internet Jan. 1, 2003 <<http://www.emsl.pnl.gov:2080/docs/msd/fticr/OTOF_Description.html>>.

Schmitt-Kopplin, Philippe et al., "Capillary elctrophoresis—mass spectrometry: 15 years of developments and applications", Electrophoresis (2003), 3837-3867.

Selby, David S., et al., "Demonstrating the effect of the 'polarised grid geometry' for orthogonal acceleration time-of-flight mass spectrometers". Rapid Communications in Mass Spectrometry (2000) 14:616-617.

Sharara, K., et al., "Development of membrane introduction mass spectrometry for monitoring trace organics in water". Water Science and Technology (2000) 41(10-11):373-380.

Vestal, M., et al., "Resolution and mass accuracy in matrix-assisted laser desorption ionization-time-of-flight". J. Am. Soc. Mass Spectrom (1998), 9:892-911.

Williams, Jon D., et al., "Using accurate mass electrospray ionization-time-of-flight mass spectrometry with in-source collision-induced dissociation to sequence peptide mixtures". Journal of Chromatography A (2003) 1020:11-26.

Zare, Richard M., et al., "Hadamard transform time-of-flight mass spectrometry: more signal, more of the time". Stanford University, Department of Chemistry, 28 pages.

Belov, Mikahil et al., "Multiplexed orthogonal time of flight mass spectrometry (MOTOF-MS)". American Society of Mass Spectrometry Annual Meeting, (2004), Nashville, TN.

Lee, Edgar D. et al., "On-line capillary zone electrophoresis-ion spray tandem mass spectrometry for the determination of dynorphins". *Journal of Chromatography* (1988), 458:313-321.

Olivares, Jose A. et al., "On-line mass spectrometric detection for capillary zone electrophoresis". *Anal. Chem.* (1987), 59:1230-1232.

Smith, Richard D. et al., "Capillary zone electrophoresis-mass spectrometry using an electrospray ionization interface". *Anal. Chem.* (1988), 60:436-441.

Stults et al., U.S. Appl. No. 10/681,742 entitled "Methods and apparatus for self-optimization of electrospray ionization devices", filed Oct. 7, 2003.

Foley et al., U.S. Appl. No. 10/703,751 entitled "Field termination grid in the ion extraction region of a multiplexed orthogonal time-of-flight mass", filed Nov. 6, 2003.

* cited by examiner

| BIOMARKER | MASS SPECTRUM FILTER PATTERN | ELUTION TIME | ELUTION/RETENTION TIME WINDOW |
|---|---|---|---|
| 1,2 | A | $t_1$ | $\Delta t_1$ |
| 3 | B | $t_2$ | $\Delta t_2$ |
| 4 | C | $t_3$ | $\Delta t_3$ |
| ... | ... | ... | ... |

US 6,958,473 B2

A-PRIORI BIOMARKER KNOWLEDGE BASED MASS FILTERING FOR ENHANCED BIOMARKER DETECTION

FIELD OF THE INVENTION

The invention relates to methods and apparatus for increasing the dynamic range and sensitivity of mass spectrometers. More specifically, the invention relates to improved performance of mass spectrometers with selective ion filtering and accumulation of desired ions that provide selected biomarker patterns based on a priori elution time intervals.

BACKGROUND OF THE INVENTION

A mass spectrometer is an analytical tool for determining the mass of sample ions based on its mass to charge ratio (m/z). A sample solution may be ionized by inducing either the loss or gain of a charge before introducing the resulting ions into a mass analyzer. The formed ions are separated afterwards according to their relative mass to charge ratios followed by detection to provide a resulting mass spectrum.

A variety of ionization techniques are available today that may be selected based upon a particular application. Each ionization technique can be specifically chosen for its unique ability to provide certain results depending upon device sensitivities and mass ranges that may be required. Electrospray ionization (ESI) for example is a method often used for analysis of molecules such as peptides, proteins and carbohydrates. A fine spray of highly charged droplets is formed in the presence of an electrical field and directed to an mass analyzer. Because a solution can be continuously introduced for analysis, ESI is particularly suitable for and often interfaced with sample preparation techniques such as liquid chromatography (LC) and capillary electrophoresis (CE). ESI is further interfaced with a variety of mass analyzers such as time-of-flight or quadrupole ion trap mass analyzers. While most mass analyzers achieve the same basic result of ion separation, each can accomplish this goal differently in that some may separate ions based on space or positioning, while others may separate ions based on time. For example, an ion trap mass analyzer traps ion species of a selected m/z ratio within a radio frequency (RF) quadrupole field. The quadrupole electric field formed inside an ion trap mass spectrometer is accomplished by applying an RF voltage so as to capture and accumulate ions before they are selectively ejected to a detector afterwards. Accumulation of ions for extended period of time enhances the signal-to-noise ratio of species delivered to an ion trap mass spectrometer by continuous flow separation techniques such as CE which may not be accomplished with other types of mass spectrometers.

The sensitivity and performance of trapping mass analyzers is known to diminish when there is a large abundance of undesired ion species within a mixture which can be referred to as background ions. The analysis of complex mixtures frequently involve the presence of only small amounts of important components amidst an abundance of relatively irrelevant ions. In order to fully recognize the potential of mass spectrometers as powerful analytical tools for biological applications, they must perform qualitative and quantitative molecular analysis of complex mixtures where the relative abundances of discernable components can vary by many orders of magnitude. For example, a major goal of research in the field of proteomics or biomarker pattern discovery calls for the highly selective analysis of many important classes of proteins which are often present in relatively low concentrations. The possible range of peptide or protein concentrations in proteomic measurements can be many orders of magnitude less in comparison to other mixture components that are not of interest. When interfaced with CE separation techniques in particular, the total number of ion species eluted and the complexity of the overall mixture itself can be significant while the relative abundance of components of interest is extremely limited. The elution of highly abundant peptides can restrict the detection of less abundant peptides eluting at or near the same time since the dynamic range of mass spectrometers can be relatively limited. In other words, the detection sensitivity for ions of interest deteriorates when there is a large amount of background ions. There is a need for solutions that enhance the dynamic range and sensitivity of ion trap mass spectrometers for analysis of complex mixtures with components having varying abundances which can differ by many orders of magnitude.

SUMMARY OF THE INVENTION

The invention provides mass spectrometers with improved sensitivity and increased dynamic range. Various aspects of the invention can be particularly applied to different types of mass analyzers and ion filters. The concepts of the invention can be applied for the mass analysis of large macromolecules and complex biological samples such as cell tissues and proteolytic digests. It shall be understood that any features of the described embodiments of the invention may be considered individually or in combination with other variations and aspects of the invention.

Method and apparatus for enhanced biomarker detection are provided in accordance with the invention by using data directed mass filtering. A mass analysis system configuration may be selected that includes a separation device that elutes multiple separation runs of ions into an ion trap mass analyzer and an ion filter. A first separation run of ions originating from the separation device may lead to an ionization source, which in turn is followed by the ion filter. The various elution times for ions of interest within the first separation run may be measured as they are eluted from the separation device to determine a priori retention time intervals for these ions of interest. All ions from the first separation run may be then directed to an ion trap mass analyzer for detection during this pre-scan procedure following an accumulation of these ions. The mass to charge (m/z) values for a mass spectrum may be thereafter measured which corresponds to both desired ion species and undesired ion species contained in the first separation run of ions. After the a priori retention time intervals for ions of interest are predetermined, a second separation run of ions may be introduced through the ion filter in a manner similar to that of the first separation run. However, the elution times for the second separation run of ions are measured to determine whether they fall within at least one a priori determined retention time interval for ions of interest so only ions of interest are filtered and pass from the ion filter into the ion trap to notch out portions of the mass spectrum corresponding to undesired ions. The ions of interest from this second separation run are allowed to accumulate within the ion trap for a predetermined period of time that is derived at least in part by measured intensities of the ions of interest in the first separation run of ions. The predetermined period for accumulation should however not exceed a priori retention time intervals for ions of interest. By focusing on selected regions of a mass spectrum corresponding to ions species of interest used to identify the presence of a biomarker, the mass analysis is performed on ions of interest that are known to elute from a separation process within predefined elution time windows. More than one biomarker can be screened for during a single elution so that a plurality of species of interest can be isolated while other undesired ions eluting at different time windows are removed.

Another embodiment of the invention provides methods and apparatus for enhanced biomarker detection based upon a priori elution retention time intervals that are predetermined. A sample may elute from a separation device into an ionization source which ionizes both desired biomarker species and undesired ion species. Elution times may be measured for the undesired ion species and the desired ion species from the separation device. These ion species may be introduced into an ion filter so that undesired ions can be filtered out with the ion filter by ejecting undesired ion species which fall outside selected a priori retention time intervals corresponding only to desired ion species which provides a tailored biomarker mass spectrum for a predetermined biomarker pattern.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

BRIEF DESCRIPTION OF THE FIGURES

The figures contained in this specification and features illustrated therein describe many of the advantages of the invention. It shall be understood that similar reference numerals and characters noted within these illustrations herein can designate the same or like features of the invention. The figures and features depicted therein are not intended to limit the scope and nature of the invention, and may not be drawn to scale.

DETAILED DESCRIPTION OF THE INVENTION

The invention provides methods and apparatus for improving the sensitivity and performance of mass spectrometers. Various aspects of the invention can be combined or applied individually as more fully described below.

Figure 1:
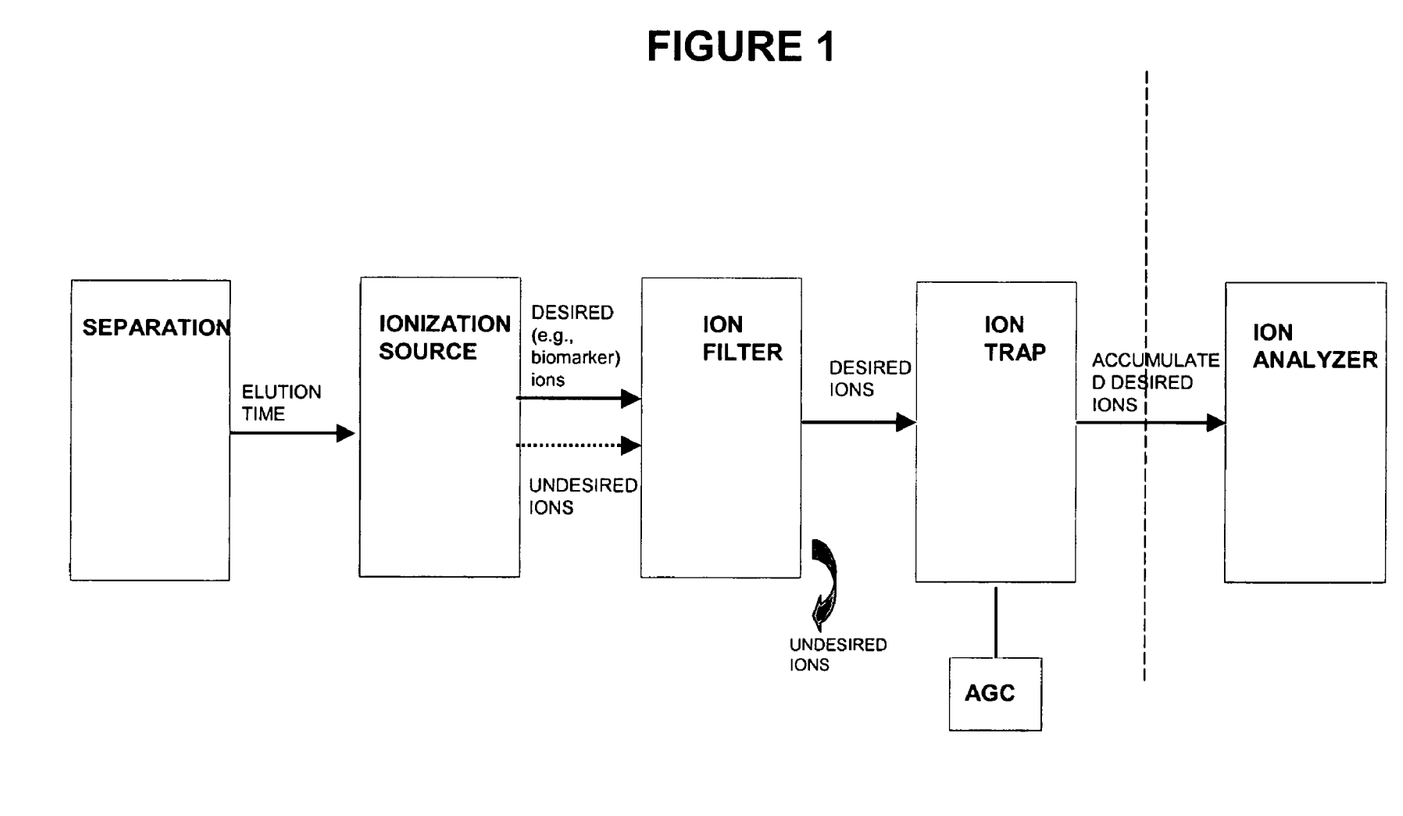
FIG. 1 provides an overall illustration of the methods and apparatus for providing enhanced biomarker pattern detection based on a priori elution retention time intervals.

FIG. 1 illustrates an embodiment of the invention that provides an ion trap mass spectrometer with an ionization source such as an electrospray ionization (ESI) source. An embodiment of the invention provides methods of enhanced biomarker detection using data directed mass filtering. These methods can be carried out on mass spectrometry systems consisting of a separation device followed by an ionization source. The ionization source may be any source conventionally used in mass spectrometry and interfaced with any conventional separation schemes such as electrophoretic or chromatographic commonly used in the field. The ions from the ionization source may be directed into an ion filter such as a quadrupole ion filter that is followed by an ion trap mass analyzer consisting of an ion trap for accumulation of ions and a detector, or in an alternative embodiment it may serve as an intermediate ion trap to externally accumulate ions before they are directed to another mass analyzer as alternatively illustrated in FIG. 1 with dashed lines. In the case where collection is an intermediate trap, the desired ions are accumulated in the intermediate trap, and then transferred to a separate mass analyzer such as a Fourier transform ion cyclotron resonance mass spectrometer (FTICR or FTMS) or time-of-flight mass spectrometer (TOFMS) where the mass analysis is performed.

A first separation run of ions or pre-scan can be initiated with the flow of a sample from the separation device as shown in FIG. 1. The elution times for various components of the sample can be detected and measured before entering the ionization source. Both the desired and undesired ions are thereafter formed by the ionization source and directed into the ion filter. At least a portion of the first separation of ions are accumulated within the ion trap portion of an ion trap mass analyzer during an initial period of time for subsequent ion detection by the detector. The mass to charge (m/z) values for a mass spectrum may be identified and correspond to both desired ion species and undesired ion species contained in the first separation run of ions. The measured elution times for ions of interest within the first separation run are identified to determine a priori retention time intervals for those ions of interest. A second separation run of ions is subsequently introduced through the ion filter immediately after the initial separation run or at some point in time in the future. The elution times for the second separation run of ions are measured to determine whether they fall within at least one of the a priori determined retention time interval for ions of interest. Only those ions of interest are permitted to pass from the ion filter into the ion trap that results in notched-out portions of the mass spectrum corresponding to undesired ions. Moreover, the ion filter can be disabled during the second separation run when elution times do not fall within at least one a priori retention time interval for ions of interest determined during the first separation run. The resulting mass spectrum of a sample can be therefore compared and analyzed for a selected biomarker pattern and corresponding ions known in advance which presumes a-priori knowledge of biomarker patterns. Moreover, during this second separation run, it is preferable that only those ions of interest are selectively accumulated in the ion trap for a predetermined period of time that is derived at least in part by measured intensities of the ions of interest in the first separation run of ions. The predetermined period of time should not however exceed a priori retention time intervals for ions of interest determined during the first separation run.

In another embodiment of the invention, the ion trap mass analyzer may include an automatic gain control (AGC) circuit, and wherein the step of accumulating the desired ions is selectively accomplished with the AGC circuit to maintain a desired density of ions within the ion trap. As with many available ion trap devices, the dynamic range of the ion traps provided in accordance with the invention can be further optimized by maintaining an appropriate number of ions within the trap region. Often times the most accurate results can be attained when the ion trap is filled with an optimal number of ions, and more particularly, with those desired biomarker ions of interest. When too few ions are present in the trap, device sensitivity can be relatively lower. At the same time, if too many ions are present in the trap, space-charge effects have been known to significantly diminish mass resolution of an ion trap when used for ion detection, or it can cause ion discrimination/fragmentation if an ion trap is employed for ion accumulation with subsequent ion detection using another mass analyzer (i.e., time-of-flight mass spectrometer or Fourier transform ion cyclotron resonance mass spectrometer). A preferable embodiment of the invention can effectively control or mitigate space-charge effects and the related loss of resolution in the ion trap based on a priori knowledge of the relative intensity of eluting species based on elution time, particularly for desired ions or species of interest. A subsequent separation run of ions directed into an ion trap can accumulate therein for a predetermined period of time derived at least in part by measured intensities for a particular ion species from a prior separation run. These selected ion species, particularly those ions of interest corresponding to a particular biomarker, can externally accumulate within an ion trap in combination with any type of mass analyzer when not carrying out this aspect of the invention with an ion trap mass analyzer. Additionally, another preferable embodiment of the invention can incorporate automatic gain control (AGC) techniques and circuits that are intended to dynamically maintain the total charge or the number of ions within an ion trap at a constant or optimal level. AGC can regulate the density of ions within an ion trap to a desired range by monitoring the intensity information from resulting mass spectra in an AGC feedback loop. Depending on the measured intensities for certain m/z values or ranges, more or less ions can be directed to the ion trap for selective accumulation. Based on a detected AGC signal, the accumulation time of ions delivered by continuous ion source such as CE/LC separations can be appropriately determined by a computer to allow desired ions to selectively accumulate at a desired level within the trap region. AGC can thus provide preferable accumulation results that can be derived from relative intensity information for preselected masses within a spectrum or broadband acquisitions that can be obtained for the purposes of only determining intensity information for the AGC feed back loop.

It shall be understood that other ionization sources may be selected for use with the invention including variations of ESI such as nanoelectrospray, nanospray and or microelectrospray techniques. When ionized molecules are generated from an ion source, the mixture includes both ion species of interest and background ions that ordinarily provide a mass spectrum with both desired portions of interest and undesired portions, respectively. An ion filter such as a quadrupole linear ion filter may be selected in accordance with the invention to filter or notch out undesired ions effectively eliminating them from the resulting mass spectrum. These background ions may be mass-selectively ejected while desired ions are directed into an ion trap prior to performing mass analysis.

Furthermore, the ion filters that can be selected herein can include a quadrupole ion filter or similar device to remove background ions before they enter the ion trap analyzer such as those described generally in U.S. Pat. Nos. 6,075,244, 5,572,022 and U.S. Patent Application Publication No. 2003/0071206 which are incorporated by reference herein in their entirety. U.S. Pat. No. 6,075,244 describes a manner of mass filtering using rf/dc quadrupole setup. Such a device has been known to transmit only a relatively narrow m/z range or single species of ions at a time. If more than one biomarkers with substantially different molecular masses migrate from a capillary electrophoresis (CE) column at the same time (i.e., are present in one mass spectrum), the rf/dc quadrupole mass filter would need to be scanned to deliver these biomarkers to an ion trap. This scanning can reduce the sensitivity for a particular biomarker that migrates from the CE column only for a limited period. The sensitivity will decrease even further for faster separations as the ratio of the scanning period to the biomarker migration time will increase. In addition, U.S. Patent Application 2003/0071206 describes an ion preselection approach based on resonant dipolar excitation/ejection of multiple species with different m/z values at the same time. This approach is capable of downloading an excitation waveform, which would selectively eject all other species from the selection quadrupole but the biomarkers. If more than one biomarker were to migrate from the CE column at the same time, all of them would be transmitted to the accumulation multipole. These aforementioned approaches nevertheless fail to offer the enhanced biomarker detection capabilities provided in accordance with invention.

After the mass filter removes background ions to better isolate selected sample ions, the sample ions can then enter into an ion trap such as a linear ion trap based on rf-only multipole (e.g., quadrupole or octopole). A linear ion trap may be employed for ion accumulation in accordance with the invention herein or other standard ion traps can be used. The ions are allowed to accumulate within the trap for a certain period of time before they are detected and analyzed. During continuous flow separation of a mixture, the desired ions are thus permitted to selectively accumulate within an ion trap for subsequent detection that improves the dynamic range and sensitivity of the mass spectrometer. Furthermore, a 3-D quadrupolar ion trap may be alternately selected which basically includes a ring electrode in between two end cap electrodes facing towards each other and aligned with the hole in the ring electrode. A radio frequency voltage is applied between the ring electrode and two end cap electrodes so as to generate a three-dimensional radio frequency quadrupole electric field between the electrodes in which ions accumulate. Mass analysis can be either performed in the same ion trap where desired ions are accumulated, or in yet another ion trap mass analyzer downstream in accordance with known tandem mass spectrometer configurations.

In an alternative embodiment of the invention, dynamic data based filtering may also be selected to remove undesired proteins from the mass spectrum. In this approach, the elution time at which to apply the desired filter is not known a-priori, but is determined dynamically as the sample is eluting and the spectrum determined "on the fly." This approach is sometimes referred to as dynamic range enhancement applied to mass spectrometry (DREAMS) and can automatically remove proteins or undesired ions that exists in relatively large abundance from those that appear in relatively fewer numbers (U.S. Patent Application Publication No. 2003/0071206 referenced above). The desired ions of interest which often but not always appear in relatively low abundances can be effectively detected to help identify the presence of certain proteins which are important in biomarker pattern studies. As compared to DREAMS approach described in the U.S. Patent Application Publication No. 2003/0071206 which expands the dynamic range of a mass spectrometer by removing the most abundant proteins in a mass spectrum while accumulating lower abundance species for extended periods of time, the present invention enables the enhancement of the signal-to-noise ratios of specific biomarker ions whose intensities may be comparable to that of the most abundant species in the acquired mass spectrum. A quadrupole ion filter or other filtering device can be selected to remove background or undesired ions based on their m/z to improve dynamic range and device sensitivity. The quadrupole ion filter can be also used with a combination of configured high/low bandpass mass filters to select a specific ion species or m/z range for detailed analysis. This targets a specific m/z peak(s) and/or defined mass range(s) to filter out excess information outside the field of interest and focuses on desired ions which may otherwise appear as relatively low abundance species. A disadvantage of DREAMS is that significantly more data processing must occur dynamically to process the spectrum and determine when to apply the appropriate mass filtering. Whereas, with the present invention, if the variation in elution times can be sufficiently controlled, no dynamic analysis of the spectrum need be performed in order to appropriately filter the eluting sample. An ion filter as described herein can be selectively applied in accordance with the invention to capture particular marker ions having certain m/z ratios within a mass spectrum that are known to elute during retention time windows determined a priori during a previous ion separation or initialization run.

Figure 2:
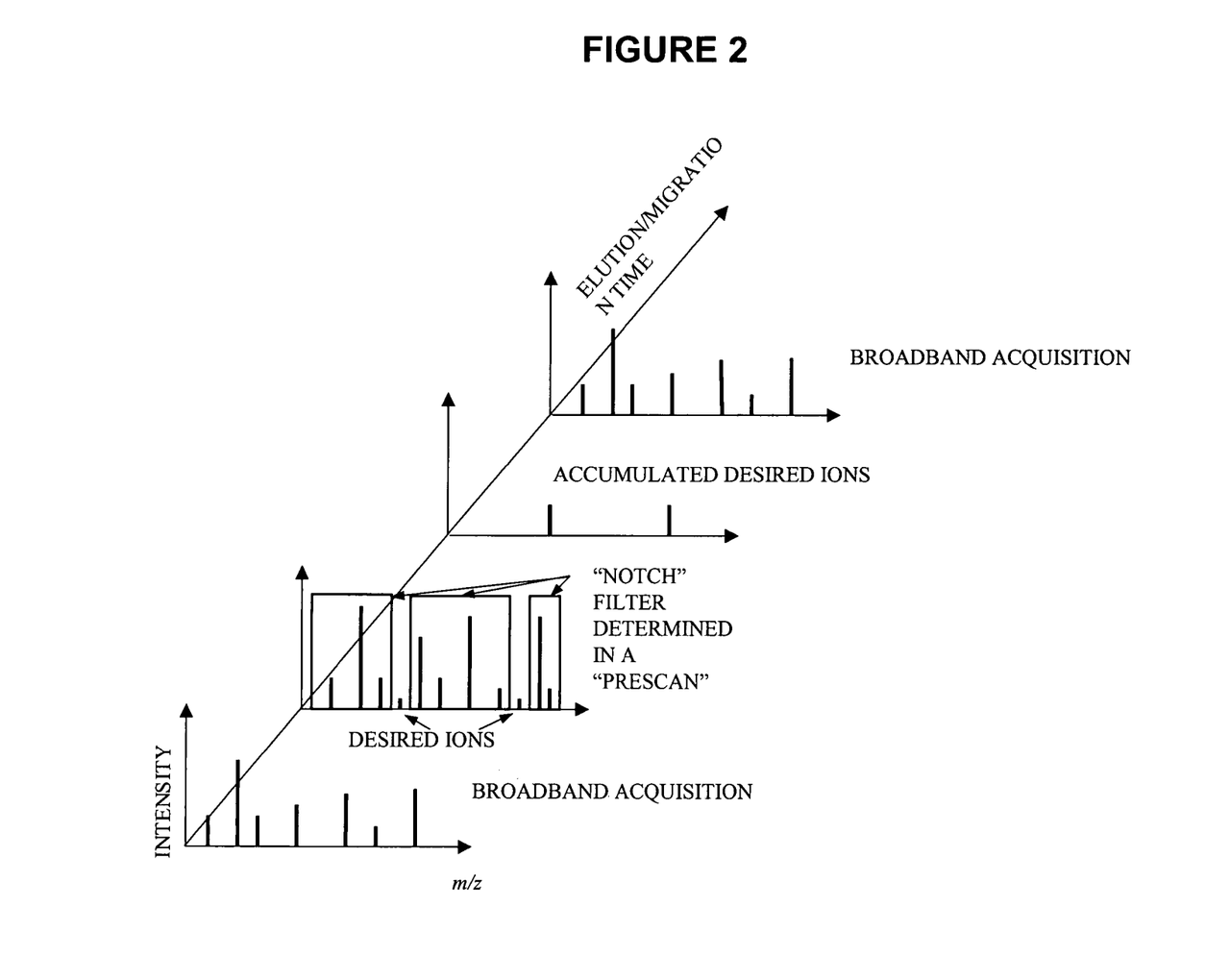
FIG. 2 includes a series of mass spectra describing both broadband acquisition of all ion species and those only for desired ions upon filtering of undesired ion species.

The undesired portions of a mass spectrum can be determined in advance and notched-out in accordance with another aspect of the invention as shown in FIG. 2. During broadband data acquisition of all ions, all ions are allowed to pass through the filter and are detected resulting in a complete mass spectrum with peaks associated with undesired ions and sometimes no observed peaks for desired ions of interest as illustrated. By identifying during a pre-scan those elution retention time intervals during which desired ions are known to elute, only those desired ions are passed through the ion filter for subsequent detection. Meanwhile, the undesired ions falling outside the defined elution windows are filtered out by the ion filter which is enabled during those timeframes. The resulting mass spectrum excludes notched-out portions corresponding to undesired ions. As a result, the ions which correspond to the undesired parts of the spectrum can be selectively removed with the ion filter at appropriate elution times in order to allow selective data acquisition for only desired ions. The desired ions can be allowed to accumulate which results in relatively greater observed intensities for a particular known biomarker pattern as shown in FIG. 2. A return cycle to a broadband acquisition may be conducted thereafter where all ion species are allowed again to pass through the ion filter to provide to a broadband mass spectrum where peaks associated with desired ions are not observed while those for undesired ions predominate.

Figure 3:
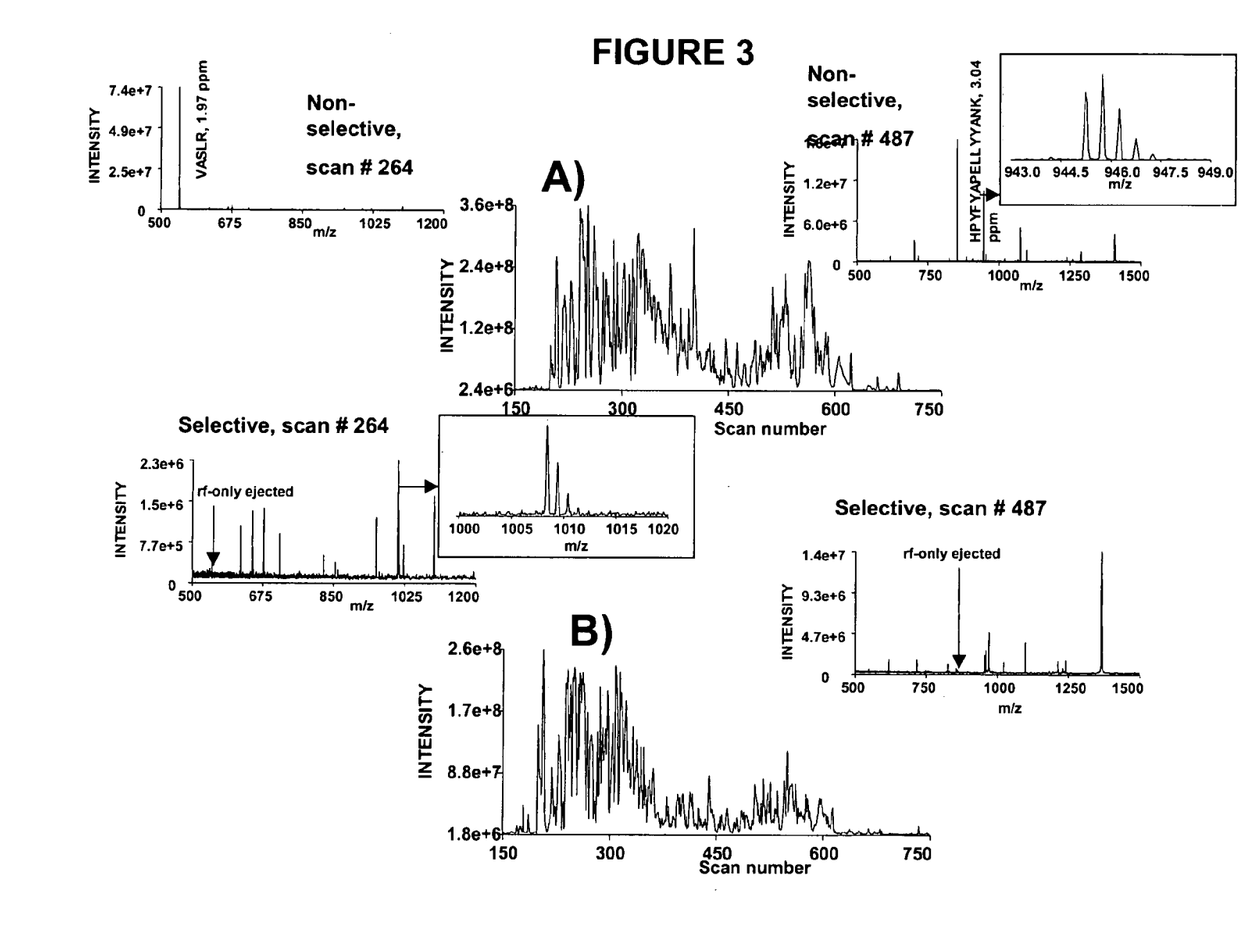
FIGS. 3A–B are comparative illustrations between non-selective scans and selective scans that eject certain abundant ion species resulting in detection of selected peaks for ions of interest.

FIGS. 3A and B are comparative illustrations of non-selective scans and selective scans. Non-selective scans (FIG. 3A) and selective scans (FIG. 3B) were alternately performed multiple times ranging from about 150 to 750 scans as shown. While ejecting certain relatively abundant ions during selective data acquisitions and ion accumulation, the resulting mass spectrum reveals certain peaks corresponding to relatively less abundant ions associated with a variety of known biomarkers. When running a scan non-selectively as shown with scan #264 in FIG. 3A, the resulting mass spectrum includes certain ions in relatively great abundance that may not be necessarily of interest such as those corresponding to the VASLR peak between m/z of 550 and 600. However when this ion species can be rf-only ejected by an ion filter because it falls outside an a priori determined elution retention time interval for a biomarker and allowed to accumulate for a predetermined elution retention time interval in accordance with the invention, those desired ions which would otherwise be unnoticed can be detected during a corresponding scan #264 in FIG. 3B as illustrated to provide a tailored mass spectrum for a particular biomarker. The appropriate rf fields can be applied to the ion filter such that the undesired ions are ejected. The ejection of undesired ions is preferably caused by resonant rf-only excitation. This resonant rf-only excitation may be dipolar, quadrupolar, or parametric. Once the undesired ions have been ejected, the desired ions can be then accumulated in an ion trap for subsequent analysis. The ion trap is preferably an ion trap mass spectrometer or a Fourier transform ion cyclotron mass spectrometer. Because of the known disadvantages for searching an entire mass spectrum for certain biomarkers of interest, this aspect of the invention accomplishes filtering out of background or undesired ions which may be present in large abundances except for certain biomarker ions of interest which are known to elute at selected times within known a priori elution retention time intervals. When elution times for a particular m/z ion species are already known, these desired ions can pass through an ion trap for subsequent accumulation within a defined elution time window to confirm the presence of the biomarker(s). Elution times therefore provide an added piece of information to enhance the sensitivity and assist in identifying one or more desired ions from those not of interest. Similarly, when running a scan non-selectively as shown with scan #487 in FIG. 3A, the HPYFYAPELLYY-ANK peak between m/z of 750 and 1000 predominates the mass spectrum. The illustrated close-up with greater resolution of this mass spectrum for the m/z range between 944.5 and 947.5 reveals five additional peaks as shown. When this relatively abundant ion species is rf-only or otherwise ejected by an ion filter as described herein, other peaks are revealed in a corresponding scan #487 in FIG. 3B. The invention thus provides selective data acquisition and ion accumulation during a priori elution retention time intervals for only those ions of interest corresponding to a known biomarker. Alternative embodiments of the invention provide methods and apparatus for a priori biomarker knowledge based mass filtering which result in tailored mass spectrum as show in FIGS. 3A and B. For example, an ion trap mass analyzer and an ion filter may be configured to detect both undesired and desired ion species during a first or initial separation run. An ion sample containing undesired ion species and desired ion species may be timed as they elute from a separation device and ionized by an ionization source. The ionization source may be followed by an ion filter that initially allows all ion species to pass which permits broadband data acquisition for all species. The elution times for the undesired ion species and the desired ion species are both measured. However the elution times for the one or more selected ions of interest associated with a biomarker are measured to define the temporal limits of an elution retention time interval. Those ions falling outside these a priori time intervals are filtered out by the ion filter which may be enabled to eject undesired ion species falling outside at least one a priori retention time interval corresponding to only desired ion species during later separation runs. Only those desired ions of interest are allowed to accumulate within a downstream intermediate ion trap or ion trap analyzer. Accordingly, such selective data acquisition and ion accumulation can provide an enhanced biomarker mass spectrum for a selected biomarker pattern with notched-out portions related to ions that are not of interest.

Figure 4:
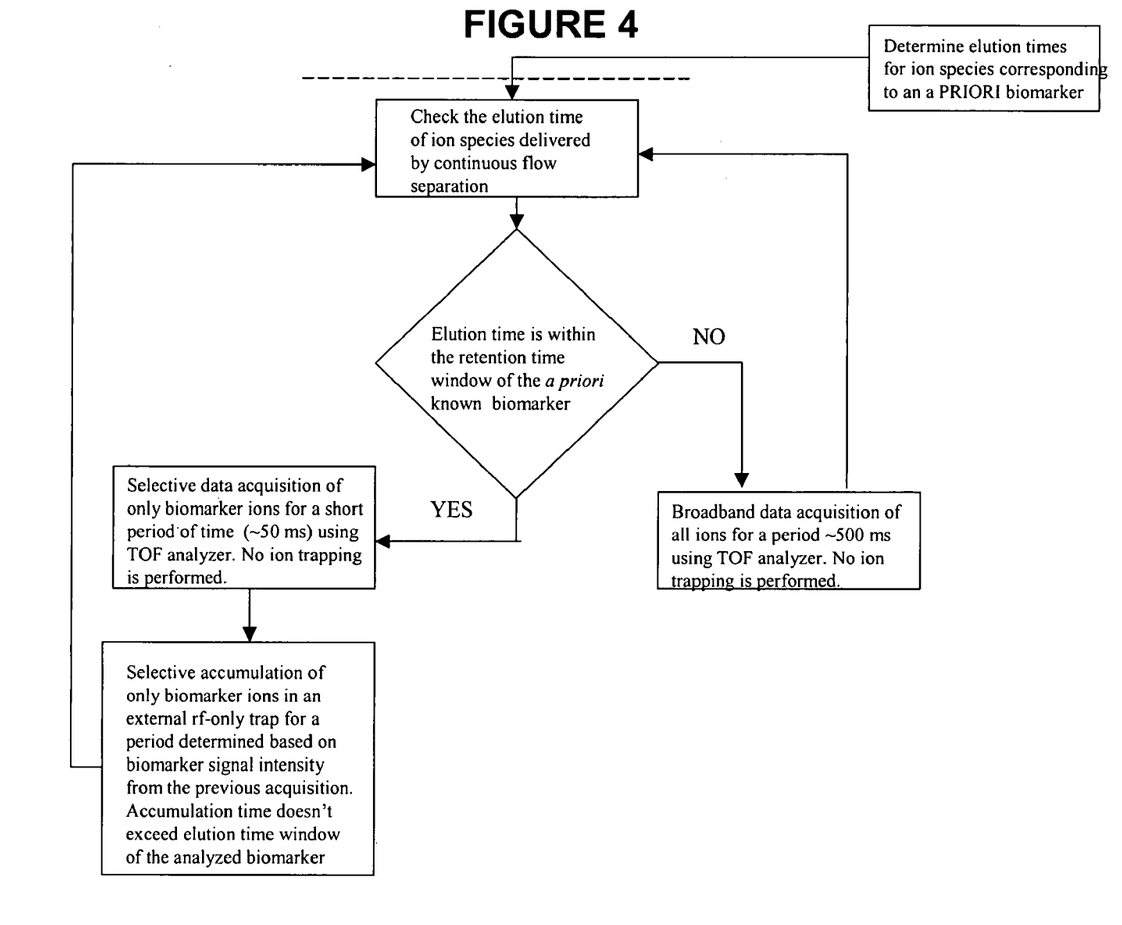
FIG. 4 is a flow diagram describing the selective data acquisition for only biomarker ions falling within predetermined elution retention time windows.

The flowchart shown in FIG. 4 illustrates another embodiment of invention and various methodologies provided in accordance with the invention for enhanced biomarker detection. During an initial separation run or pre-scan for selected biomarkers, elution retention time intervals may be determined by detecting and measuring when desired biomarker ion species for one or more selected biomarkers begin to elute from a separation device. The data from this separation run may be determined for another separation run to be conducted immediately thereafter, or stored in a computer database in accordance with another aspect of the invention or otherwise retained for later use during separation runs to be completed sometime in the future. These a priori elution retention time intervals may include a single or multiple periods of time typically ranging 50 ms to 500 ms or greater which correspond to one or more selected group of biomarker ions.

Upon the determination of elution times for selected ion species which correspond to a selected a priori known biomarker beforehand, a separation run may be conducted as described elsewhere herein to elute a sample solution into an ionization device such as an ESI microfluidic chip. For example, the elution times for various ion species are checked and measured during a continuous flow separation. These ion species include both desired biomarker ions along with those undesired ion species that are typically present in great abundance. When the measured elution time falls within an a priori elution retention time interval corresponding to the selected biomarker(s), only those desired ions during this period of time are passed through the ion filter and ion trap. Upon detection, selective data acquisition is achieved for only those biomarker ions that elute during a relatively short and defined period of time. This time period in which desired ions are eluted can range up to and around approximately 50 ms. Various types of mass analyzers may be selected with the invention including time-of-flight (TOF) mass analyzers wherein ion trapping is not performed preferably during this initial separation run or pre-scan. Meanwhile, for ions that elute at other times falling outside the time window associated with the predetermined biomarker pattern, broadband data acquisition is achieved for all ions eluted during a relatively longer and defined period of time. The period of time for broadband data acquisition may extend up to and over 500 ms with mass analyzer devices such as TOF analyzers. Again no ion trapping is performed during this initial pre-scan. During a subsequent mass spectrum acquisition, only those desired biomarker ions known to elute during a priori elution time intervals can be accumulated selectively for a predetermined period of time inside an external rf-only ion trap, or alternatively, within the ion trap portion of an ion trap mass analyzer. This period of time for selective accumulation may be determined based on biomarker signal intensity for desired ions obtained from the previous acquisition. The accumulation time for these desired biomarker ions should preferably not exceed the elution time window determined for the selected corresponding biomarker. It shall be further noted that the ions identified for ejection during subsequent separation runs following a pre-scan will typically be the most highly abundant species. The ejection of these species often times produce the most additional capacity for further accumulation in the ion trap for desired ions. However, it may not always be the case that ions are selected for ejection based purely on their abundance. In certain applications, ions are selected simply because they are not of interest to the desired analysis, even though they are not the most abundant. The present invention should thus be broadly-construed to include any application where ions are selectively ejected by the ion filter using rf excitation or similar methods to make room for further accumulation.

Figure 5:
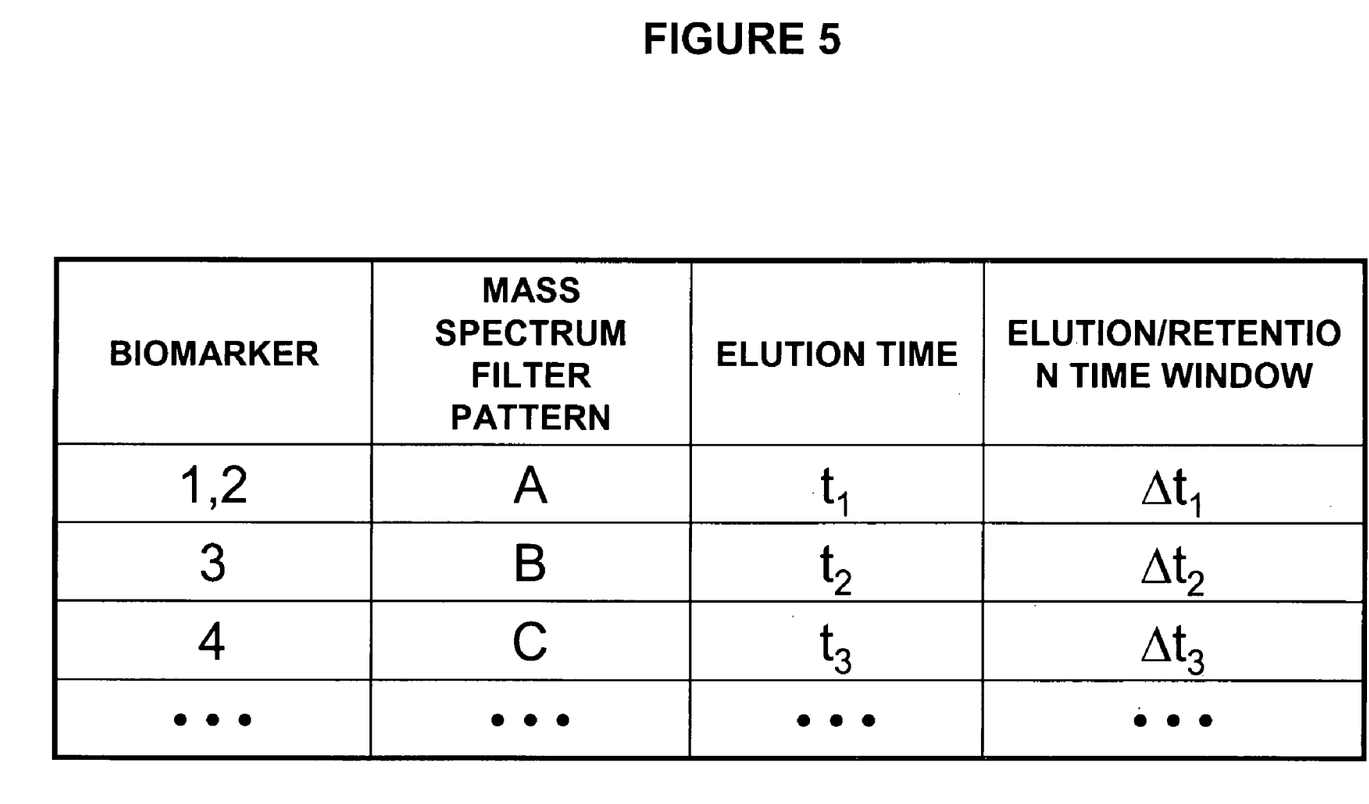
FIG. 5 is a table of elution time windows for selected biomarker ions that elute from a separation device at measured elution times excluding undesired ion species that are filtered out in accordance with a predetermined mass spectrum filter pattern.

FIG. 5 illustrates an elution retention time table provided in accordance with another aspect of the invention. The elution retention times corresponding to various biomarkers can be compiled in a database comprising a plurality of data sets for each biomarker (biomarker 1–4 or greater), wherein each data set includes a corresponding mass spectrum filter pattern (A–C or greater). Each dataset may include more than one biomarker (1,2) as illustrated. The elution times ($t_1$–$t_3$ or greater) for selected biomarker ions can be determined ahead of time and included within the datasets for each biomarker. This elution time/mass spectral computer database may be generated ahead of time during an initial ion separation run for particular biomarkers. The data may include predetermined elution times and time windows or intervals derived from standardized conditions for desired m/z proteins which provide certain biomarker patterns. The standardization of elution conditions can minimize or avoid large variations in elution times since similar operating parameters are be selected. Variations in elution times and intervals could otherwise occur and are attributable to numerous factors such as variations in CE temperature and electroosmotic flow. In order to define a priori elution retention time intervals or windows corresponding to desired biomarker ion species, a pre-scan or initial separation run may be conducted to identify and measure the elution times and ranges for desired ion species. During this period of time, desired ion species pass through the ion filter into an ion trap as described herein. Each retention time window may be defined and begin around the time a first known desired ion species is known to elute from a separation device. The respective time windows can also terminate or end at a time at which desired ion species corresponding to a biomarker pattern no longer elute from the separation device. During an initial separation run, undesired ion species are identified and their respective elution times are measured too and pass through the ion filter and ion trap. Following detection of all ion species in either the ion trap itself or a separate mass analyzer, a complete mass spectrum is provided. When selected portions of the mass spectrum corresponding to undesired ion species are identified which can be notched-out, a mass spectrum filter pattern may be constructed to filter out undesired ion species thus allowing only desired biomarker ions to pass through the ion filter during a subsequent separation run. Only those ions corresponding to selected elutions times for a particular biomarkers falling within the selected a priori elution retention time windows are allowed through the ion filter and subsequently detected. An enhanced biomarker mass spectrum pattern may be thus provided which excludes or has notched-out portions of the mass spectrum corresponding to ions other than desired biomarker ions of interest. It shall be understood that the elution time/mass spectral database can be alternatively constructed and searched to identify certain biomarker ions of interest according to their characteristic elution times. These ions can be identified based on specific times in which they are known to elute within pre-defined elution time windows.

While the invention has been described with reference to the aforementioned specification, the descriptions and illustrations of the preferable embodiments herein are not meant to be construed in a limiting sense. It shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art upon reference to the present disclosure. It is therefore contemplated that the appended claims shall also cover any such modifications, variations and equivalents.

What is claimed is:

1. A method of enhanced biomarker detection using data directed mass filtering comprising the steps of:
   selecting an ion trap mass analyzer and an ion filter;
   introducing a first separation run of ions from a separation device and ionization source into the ion filter and followed by the ion trap mass analyzer which includes an ion trap and a detector;
   accumulating at least a portion of the first separation of ions within the ion trap for an initial period of time for subsequent ion detection by the detector;
   measuring mass to charge (m/z) values for a mass spectrum corresponding to desired ion species and undesired ion species contained in the first separation run of ions;
   measuring elution times for ions of interest within the first separation run eluted from the separation device to determine a priori retention time intervals for ions of interest;
   introducing a second separation run of ions through the separation device and into the ion filter;
   measuring elution times for the second separation run of ions to determine whether they fall within at least one a priori determined retention time interval for ions of interest so only ions of interest are filtered and pass from the ion filter into the ion trap to notch out portions of the mass spectrum corresponding to undesired ions; and
   accumulating only the ions of interest within the second separation run of ions in the ion trap for a predetermined period of time that is derived at least in part by measured intensities of the ions of interest in the first separation run of ions, and wherein the predetermined period of time does not exceed a priori retention time intervals for ions of interest determined during the first separation run.

2. The method as recited in claim 1, wherein filtering by the ion filter is disabled during the second separation run when elution times do not fall within at least one a priori retention time interval for ions of interest determined during the first separation run.

3. The method as recited in claim 1, wherein the ion trap mass analyzer includes an automatic gain control (AGC) circuit, and wherein the step of accumulating the desired ions is selectively accomplished with AGC to maintain a desired density of ions within the ion trap.

4. The method as recited in claim 1, wherein the ion filter is a quadrupole linear ion filter.

5. A method of enhanced biomarker detection using data directed mass filtering comprising the steps of:
   selecting an ion filter configured in a predetermined arrangement with an ion trap followed by a mass analyzer;
   introducing a first separation run of ions from a separation device and ionization source into the ion filter and then through the ion trap followed by the mass analyzer for detection of at least a portion of the first separation run of ions;
   measuring mass to charge (m/z) values for a mass spectrum corresponding to desired ion species and undesired ion species contained in the first separation run of ions;
   measuring elution times for ions of interest within the first separation run eluted from the separation device to determine a priori determined retention time interval for ions of interest;
   introducing a second separation run of ions through the separation device and into the ion filter; and
   measuring elution times for the second separation run of ions to determine whether they fall within at least one a priori determined retention time interval for only ions of interest so only ions of interest are filtered and passed from the ion filter onto the ion trap followed by the mass analyzer which provides notching out of portions of the mass spectrum corresponding to undesired ion species.

6. The method as recited in claim 5, wherein only the ions of interest within the second separation run of ions are accumulated in the ion trap for a predetermined period of time that is derived at least in part by measures intensities of the ions of interest from the first separation run of ions, wherein the predetermined period of time does not exceed the selected a priori retention time interval for ions of interest.

7. The method as recited in claim 5, wherein no accumulation of any ions within the second separation run is performed when elution times for the second separation run do not fall within at least one a priori determined retention time interval for the ions of interest to provide broadband acquisition of ions from the second separation run.

8. The method as recited in claim 5, wherein filtering by the ion filter is disabled when elution times for the second separation run do not fall within at least one a priori determined retention time for ions of interest.

9. The method as recited in claim 5, wherein both desired and undesired ions are allowed to pass through the ion filter when elution times for the second separation run of ions do not fall within at least one a priori determined retention time for ions of interest.

10. The method as recited in claim 5, wherein the mass analyzer includes an automatic gain control (AGC) circuit for monitoring intensity information derived from the mass spectrum, and wherein the step of externally accumulating the desired ions is selectively accomplished with AGC to maintain a desired density of ions within the ion trap.

11. The method as recited in claim 5, wherein the mass analyzer is a FTMS device.

12. The method as recited in claim 5, wherein the mass analyzer is a TOF mass analyzer.

13. A method for a-priori biomarker knowledge based mass filtering comprising the following steps of:

selecting an ion trap mass analyzer and an ion filter;

eluting an ion sample containing undesired ion species and desired ion species from a separation device that is ionized by an ionization source followed by the ion filter;

measuring elution times for the undesired ion species and the desired ion species from the separation device; and filtering out undesired ions with the ion filter by ejecting undesired ion species which fall outside at least one a priori retention time interval corresponding to only desired ion species to provide a tailored biomarker mass spectrum for a predetermined biomarker pattern.

14. The method as recited in claim 13, wherein the tailored biomarker mass spectrum pattern excludes portions corresponding to undesired ion species that are notched-out.

* * * * *